(12) United States Patent
Okamoto et al.

(10) Patent No.: US 8,269,038 B2
(45) Date of Patent: Sep. 18, 2012

(54) PROCESS FOR PRODUCTION OF SULFONIC ACID ESTER

(75) Inventors: Kuniaki Okamoto, Kawagoe (JP); Tsutomu Watahiki, Kawagoe (JP); Motoshige Sumino, Kawagoe (JP); Takao Shibasaki, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 664 days.

(21) Appl. No.: 12/441,004

(22) PCT Filed: Apr. 20, 2007

(86) PCT No.: PCT/JP2007/058607
§ 371 (c)(1),
(2), (4) Date: Mar. 12, 2009

(87) PCT Pub. No.: WO2008/032463
PCT Pub. Date: Mar. 20, 2008

(65) Prior Publication Data
US 2010/0041916 A1    Feb. 18, 2010

(30) Foreign Application Priority Data
Sep. 12, 2006  (JP) .................... 2006-246236

(51) Int. Cl.
*C07D 487/00* (2006.01)
*C07C 309/00* (2006.01)
(52) U.S. Cl. ............. 562/46; 532/1; 532/30; 532/101
(58) Field of Classification Search .......... None
See application file for complete search history.

(56) References Cited

U.S. PATENT DOCUMENTS

| | | | |
|---|---|---|---|
| 3,164,608 A * | 1/1965 | Blaser ......................... 549/40 |
| 4,666,633 A | 5/1987 | Yuki et al. | |
| 4,925,950 A | 5/1990 | Massonneau et al. | |
| 5,023,361 A | 6/1991 | Massonneau et al. | |
| 6,395,918 B1 | 5/2002 | Loewenthal et al. | |
| 2004/0152889 A1 | 8/2004 | Thaper et al. | |
| 2005/0085655 A1 * | 4/2005 | Schmidt et al. ............. 558/44 |

FOREIGN PATENT DOCUMENTS

| | | |
|---|---|---|
| CA | 1267903 | 4/1990 |
| CA | 1292236 | 11/1991 |
| JP | 49-17573 B1 | 5/1974 |
| JP | 7-33709 | 2/1995 |
| JP | 11-246514 A | 9/1999 |
| JP | 2005-336155 A | 12/2005 |
| WO | 85/03075 A1 | 7/1985 |
| WO | WO 85/03075 A1 | 7/1985 |

OTHER PUBLICATIONS

Beard, C. et al., "Synthesis of some novel trifluoromethanesulfonates and their reactions with alcohols," J.Org.Chem (1973) 38: 3673-7.*
Scoggins, M., et al., "Rapid separation technique for mono- and disulfonic acids," Anal.Chem., (1968) 40:1155-7.*
Sekera, V. et al. "Higher alkyl sulfonates," JACS, (1933) 55:345-349.*
Tipson, R., "On esters of p-toluenesulfonic acid," J. Org. Chem. (1944) 9:235-241.*
Emmons, W. et al. "Metathetical reactions of silver salts in solution. II. The synthesis of alkyl sulfonates," JACS (1953) 75: 2257.*
Mustafa, A., "The chemistry of sultones and sultams," Chem. Rev. (1954) 54: 195-223.*
Zuffanti, S., et al. "The preparation of some alkane-a,w-disulfonic acids," JACS (1941) 63: 2999-3000.*
Bauer, J. et al. "A study of methylenedisulfonic acid and its derivatives," J.Am.Pharm.Assn. (1937) 26: 485-93.*
King. J. F. and Aslam, M., "Alkylation of sulfonate anions via substrate-reagent ion-pair (SRIP) reactions of [2]betylates. Preparation of alkyl esters of hydroxyalkanesulfonic acids," Tetrahedron Letters, vol. 22, No. 37, p. 3573-3576 (1981).
King. J. F., et al., "Betylates. 3. Preparative Nucleophilic Substitution by Way of [2]-, [3]-, and [4]Betylates. Stoichiometric Phase Transfer and Substrate-Reagent Ion-Pair (SRIP) Reactions of Betylates," J. Am. Chem. Soc., vol. 104, p. 7108-7122 (1982).
Howells, R. D. and J. D. McCown, "Trifluoromethanesulfonic Acid and Derivatives," Chemical Reviews, vol. 1, p. 69-92 (1977).
International Search Report of PCT/JP2007/058607, dated May 22, 2007.
Bulletin de la Societe Chemique de France, 1977, No. 5-6, pp. 483-484.

* cited by examiner

*Primary Examiner* — Porfirio Nazario Gonzalez
*Assistant Examiner* — James Meadows
(74) *Attorney, Agent, or Firm* — Hamre, Schumann, Mueller & Larson, P.C.

(57) ABSTRACT

The present invention provides a method for producing a sulfonate ester efficiently and in high yield.
The present invention is an invention of a method for producing a sulfonate ester compound, which comprising reacting:
(a) a compound having a sulfo group ($—SO_3H$); and
(b) a compound having a group represented by the general formula [1]:

$$—OR^1 \qquad [1]$$

[wherein, $R^1$ represents a sulfonyl group represented by the general formula [2]:

$$—SO_2—R^2 \qquad [2]$$

(wherein, $R^2$ represents a halogen atom, a haloalkyl group, an alkoxy group, or an optionally substituted alkyl group or an optionally substituted aryl group) or an acyl group represented by the general formula [3]:

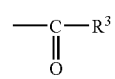

[3]

(wherein, $R^3$ represents an optionally substituted alkyl group or an optionally substituted aryl group)];
in the presence of an organic base which is capable of forming a salt with said sulfo group.

15 Claims, No Drawings

PROCESS FOR PRODUCTION OF SULFONIC ACID ESTER

TECHNICAL FIELD

The present invention relates to a method for producing a sulfonate ester.

BACKGROUND ART

Cyclic disulfonate esters have been widely used, for example, as a therapeutic agent for leukemia.

Production of cyclic disulfonate esters had been conventionally carried out by a method in which an alkanedisulfonyl chloride is reacted with silver carbonate to form a corresponding silver alkanedisulfonate, and subsequently the resultant silver alkanedisulfonate is reacted with a dihaloalkane (Patent Document 1). However, this method had problems such as costly due to necessity to use silver carbonate; inefficient due to a long reaction time; and low yield of cyclic disulfonate ester to be obtained.

Therefore, as an improved method, another method had been developed in which an alkanedisulfonic anhydride, an alkanedisulfonic acid and/or a halogenated sulfonylalkanesulfonic acid is reacted with a diacyloxyalkane or a disulfonyloxyalkane (Patent Document 2).

However, this method was not necessarily satisfactory one because it had problems such as low isolated yield due to complicated procedures, although yield of cyclic disulfonate ester had been improved compared with that of the conventional method.

On the other hand, monosulfonate esters have been widely used for various functional materials (including polymers) such as, for example, alkylating agents, acid generating agents, medical products, agricultural chemicals, colorants, electrolyte materials, as well as intermediates for their syntheses.

As a method for producing monosulfonate ester, for example, a method had been known in which a sulfonic acid and a thionyl chloride are reacted to form a sulfonyl chloride, which is then reacted with a hydroxyl compound such as, for example, methanol in the presence of a basic catalyst such as, for example, pyridine, triethylamine, sodium hydroxide (Patent Document 3).

However, this method had such problems due to by-product of hydrochloric acid, for example, that when an unsaturated aliphatic sulfonic acid such as allyl sulfonic acid is esterified, a desired sulfonate ester cannot be obtained because the raw material is hydrochlorinated by hydrochloric acid generated as a by-product; and that production at an industrial scale is risky because hydrochloric acid is produced as a by-product in the reaction system; and the like.

Under such circumstances, development of a method for producing desired various types of sulfonate esters in high yield efficiently is demanded.

[Patent Document 1] JP-B-5-44946
[Patent Document 2] JP-A-2005-336155
[Patent Document 3] JP-A-11-246514

DISCLOSURE OF INVENTION

Problems to be Solved by the Invention

The present invention has been made considering the above-exemplified circumstances, and an object of the present invention is to provide a method for producing a sulfonate ester efficiently and in high yield.

Means for Solving the Problems

The present invention is an invention of a method for producing a sulfonate ester compound, which comprising reacting:
(a) a compound having a sulfo group ($—SO_3H$); and
(b) a compound having a group represented by the general formula [1]:

$$—OR^1 \quad [1]$$

[wherein, $R^1$ represents a sulfonyl group represented by the general formula [2]:

$$—SO_2—R^2 \quad [2]$$

(wherein, $R^2$ represents a halogen atom, a haloalkyl group, an alkoxy group, an optionally substituted alkyl group or an optionally substituted aryl group) or an acyl group represented by the general formula [3]:

(wherein, $R^3$ represents an optionally substituted alkyl group or an optionally substituted aryl group)]; in the presence of an organic base which is capable of forming a salt with said sulfo group.

Effect of the Invention

According to the method for producing a sulfonate ester of the present invention, various types of sulfonate esters can be produced at low cost and efficiently in high yield, without suffering with the problems which conventional method had possessed, such as, for example, high production cost, low yield, long reaction time, many steps, limited types of starting materials which can be esterified, undesirable as an industrial production method.

BEST MODE FOR CARRYING OUT THE INVENTION

The compound having a sulfo group of (a) includes those capable of forming a salt with an organic base, for example, those represented by the general formula [4]:

$$R^4—SO_2—OH \quad [4]$$

(wherein, $R^4$ represents an optionally substituted, alkyl group, hetero-atom-containing alkyl group, alkenyl group, alkynyl group, aryl group or heterocyclic group).

Among the compounds represented by the general formula [4], a preferable specific example of the compound represented by the general formula [4], in which $R^4$ is a substituted, alkyl group or hetero-atom-containing alkyl group, and the substituent is introduced in the end of said alkyl group or hetero-atom-containing alkyl group, and the substituent is a sulfo group, includes, for example, a disulfonic acid represented by the general formula [6]:

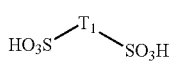

(wherein, $T_1$ represents a substituted or unsubstituted alkylene chain which may have a hetero atom in the chain, or a substituted or unsubstituted arylene chain).

On the other hand, the compound having a group represented by the general formula [1] of (b) includes, for example, those represented by the general formula [5]:

$$R^5—O—R^1 \quad [5]$$

(wherein, $R^5$ represents an optionally substituted, alkyl group, hetero-atom-containing alkyl group, alkenyl group, alkynyl group, aryl group or heterocyclic group, and $R^1$ is same to the above).

Among the compounds represented by the general formula [5], a preferable specific example of the compound represented by the general formula [5], in which $R^5$ is a substituted, alkyl group or hetero-atom-containing alkyl group, and the substituent is introduced in the end of said alkyl group or hetero-atom-containing alkyl group, and the substituent is the group represented by the above general formula [1], includes, for example, a compound represented by the general formula [7]

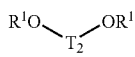

(wherein, $T_2$ represents a substituted or unsubstituted alkylene chain, which may have a hetero atom in the chain, and $R^1$ is same to the above).

It should be noted that two $R^1$ groups in the general formula [7] may be the same or different from each other.

In addition, the compound having a sulfo group of (a) and the compound having a group represented by the general formula [1] of (b) in the specification of the present application also includes those containing said sulfo group and the group represented by the general formula [1] in the same compound, and a specific example of these compounds includes, for example, those represented by the general formula [8]:

(wherein, $T_3$ represents a substituted or unsubstituted alkylene chain which may have a hetero atom in the chain, or a substituted or unsubstituted alkenylene chain, and $R^1$ is same to the above).

In the general formula [2], the halogen atom represented by $R^2$ includes, for example, a fluorine atom, a chlorine atom, a bromine atom, an iodine atom, and the like, and among them, a chlorine atom or a bromine atom are preferable, and a chlorine atom is particularly preferable.

The haloalkyl group represented by $R^2$ may be any of linear, branched or cyclic, and includes those in which a part or all of hydrogen atoms in the alkyl group having generally 1 to 12, preferably 1 to 6, and more preferably 1 to 3 carbon atoms are substituted by a halogen atom (for example, a fluorine atom, a bromine atom, a chlorine atom, an iodine atom, and the like are included, and among them a fluorine atom is preferable). Specifically, the haloalkyl group includes, for example, a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, a 2-bromoethyl group, a pentaiodoethyl group, a pentachloroethyl group, a pentafluoroethyl group, a pentabromoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonabromobutyl group, a 5-fluoropentyl group, a 5-chloropentyl group, a 5-bromopentyl group, a 2,2,3,3,4,4,5,5-octafluoropentyl group ($—CH_2(CF_2)_4H$), a 2,2,3,3,4,4,5,5-octachloropentyl group ($—CH_2(CCl_2)_4H$), a 2,2,3,3,4,4,5,5-octabromopentyl group ($—CH_2(CBr_2)_4H$), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group ($—(CH_2)_2(CF_2)_7CF_3$), a 3,3,4,4,5,5,6,6,7,7,8,8,9,9,10,10,10-heptadecachlorodecyl group ($—(CH_2)_2(CCl_2)_7CCl_3$), a 3,3,4,4,5,5,6,6,7,7,8,8,9,9,10,10,10-heptadecabromodecyl group ($—(CH_2)_2(CBr_2)_7CBr_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group, a perbromododecyl group, and the like. Among them, a perfluoroalkyl group having 1 to 3 carbon atoms is preferable, in particular, a trifluoromethyl group is more preferable.

The alkoxy group represented by $R^2$ may be any of linear, branched or cyclic, and includes those having generally 1 to 12 carbon atoms, preferably 1 to 6 carbon atoms, and more preferably 1 to 3 carbon atoms. Specifically the alkoxy group includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 1-methylpentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a cyclopropoxy group, a cyclobutoxy group, a cyclopentyloxy group, a cyclohexyloxy group, a cycloheptyloxy group, a cyclooctyloxy group, a cyclononyloxy group, a cyclodecyloxy group, a cycloundecyloxy group, a cyclododecyloxy group, and the like. Among them, for example, a methoxy group, an ethoxy group, a n-propoxy group, and the like are preferable.

In the general formulas [2] and [3], the alkyl group of the optionally substituted alkyl group represented by $R^2$ and $R^3$ may be any of linear, branched, or cyclic, and includes those having generally 1 to 12, preferably 1 to 6, and more preferably 1 to 3 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like. Among them, for example, a methyl group, an ethyl group, and a n-propyl group are preferable, and a methyl group is more preferable above all.

The aryl group of the optionally substituted aryl group represented by $R^2$ and $R^3$ includes those having generally 6 to 14, and preferably 6 to 10 carbon atoms. Specifically, the aryl group includes, for example, a phenyl group, a naphthyl group, a phenanthryl group, an anthryl group, and the like, among them, a phenyl group is preferable.

In the general formula [2], the substituent of the optionally substituted alkyl group represented by $R^2$ includes, for example, alkoxy group having 1 to 12 carbon atoms, an acyl group, a nitro group, a hydroxyl group, a carboxyl group, a cyano group, a formyl group, and the like.

In the general formula [3], the substituent of the optionally substituted alkyl group represented by $R^3$ includes, for example, a halogen atom, an alkoxy group having 1 to 12 carbon atoms, an acyl group, a nitro group, a hydroxyl group, a carboxyl group, a cyano group, a formyl group, and the like.

The substituent of the optionally substituted aryl group represented by $R^2$ and $R^3$ includes, for example, a halogen atom, an alkyl group having 1 to 12 carbon atoms, an alkoxy group having 1 to 12 carbon atoms, an acyl group, a nitro group, a hydroxyl group, a carboxyl group, a cyano group, a formyl group, and the like.

The alkoxy group having 1 to 12 carbon atoms exemplified as the substituent may be any of linear, branched or cyclic, and includes those having generally 1 to 12, preferably 1 to 6, and more preferably 1 to 3 carbon atoms. Specifically, the alkoxy group includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a cyclopropoxy, a cyclobuthyloxy group, a cyclopenthyloxy group, a cyclohexyloxy group, a cycloheptyloxy group, a cyclooctyloxy group, a cyclononyloxy group, a cyclodecyloxy group, a cycloundecyloxy group, a cyclododecyloxy group, and the like.

Among them, for example, a methoxy group, an ethoxy group, a n-propoxy group, and the like are preferable.

The acyl group exemplified as the substituent includes those having generally 2 to 20 carbon atoms derived from carboxylic acids. Specifically, the acyl group includes those derived from aliphatic carboxylic acids such as, for example, an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, a dodecanoyl group, a tridecanoyl group, a tetradecanoyl group, a pentadecanoyl group, a hexadecanoyl group, a heptadecanoyl group, an octadecanoyl group, a nonadecanoyl group and an icosanoyl group; and those derived from aromatic carboxylic acids such as, for example, a benzoyl group and a naphthoyl group. The halogen atom exemplified as the substituent includes, for example, a fluorine atom, a chlorine atom, a bromine atom, an iodine atom, and the like. Among them, a fluorine atom, iodine atom, and the like are preferable.

The alkyl group having 1 to 12 carbon atoms exemplified as the substituent may be any of linear, branched or cyclic, and includes those having generally 1 to 12, preferably 1 to 6, and more preferably 1 to 3 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like. Among them, a methyl group, an ethyl group, a n-propyl group, an isopropyl group, and the like are preferable.

Among $R^2$ in the general formula [2], a halogen atom or a haloalkyl group are more preferable, and a halogen atom is particularly preferable.

A representative example of the sulfonyl group represented by the general formula [2] includes, for example, a chlorosulfonyl group, a methanesulfonyl group (a mesyl group), a p-toluenesulfonyl group (a tosyl group), a trifluoromethanesulfonyl group (a trifle group), a chloromethanesulfonyl group, a methoxysulfonyl group, and the like.

A representative example of the acyl group represented by the general formula [3] includes, for example, an acetyl group, a pivaloyl group, a trifluoroacetyl group, a benzoyl group, and the like.

In the general formulas [4] and [5], the alkyl group of the optionally substituted alkyl group represented by $R^4$ and $R^5$ may be any of linear, branched or cyclic, and includes those having generally 1 to 12, preferably 1 to 6, and more preferably 1 to 3 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like.

In the general formulas [4] and [5], the optionally substituted hetero-atom-containing alkyl group represented by $R^4$ and $R^5$ includes those containing generally 1 to 6 and preferably 1 to 4 hetero atoms in the chain of the optionally substituted alkyl group. Specifically, the alkyl group includes, for example, those represented by the general formula [9]:

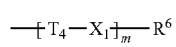

[9]

{wherein, $R^6$ represents an optionally substituted alkyl group, m pieces of $T_4$ represent each independently an optionally substituted alkylene chain having 1 to 8 carbon atoms, m pieces of $X_1$ represent each independently an oxygen atom, a sulfur atom or a group represented by the general formula [25]:

[25]

(wherein, $R^7$ represents an alkyl group, a haloalkyl group, an aryl group or an aralkyl group), and m represents an integer of 1 to 6.}

In the general formula [9], the alkyl group of the optionally substituted alkyl group represented by $R^6$ may be any of linear, branched or cyclic, and includes those having 1 to 12, preferably 1 to 6, and more preferably 1 to 3 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like.

The alkylene chain of the optionally substituted alkylene chain having 1 to 8 carbon atoms represented by $T_4$ includes linear alkylene chains having generally 1 to 8, and preferably 1 to 3 carbon atoms. Specifically, the alkylene chain includes a methylene group, an ethylene group, a trimethylene group, a tetramethylene group, a pentamethylene group, a hexamethylene group, a heptamethylene group, an octamethylene group, and the like.

The substituent of the optionally substituted alkyl group represented by $R^6$ and the substituent of the optionally substituted alkylene chain having 1 to 8 carbon atoms represented by $T_4$ include, for example, a group represented by the above general formula [1], a halogen atom, a haloalkyl group, an alkyl group, an aryl group, an alkoxy group, an acyl group, a nitro group, a hydroxyl group, a carboxyl group, a cyano group, a formyl group, a sulfo group, and the like.

The halogen atom exemplified as the substituent includes, for example, a fluorine atom, a chlorine atom, a bromine atom, an iodine atom, and the like.

The haloalkyl group exemplified as the substituent may be any of linear, branched or cyclic, and includes, for example, those in which a part or all of hydrogen atoms in the alkyl group having 1 to 12, preferably 1 to 6, and more preferably 1 to 3 carbon atoms are substituted by a halogen atom (for example, a fluorine atom, a chlorine atom, a bromine atom, an iodine atom, and the like are included, and a fluorine atom is particularly preferable). Specifically the haloalkyl group includes, for example, a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, a 2-bromoethyl group, a pentafluoroethyl group, a pentachloroethyl group, a pentabromoethyl group, a pentaiodoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonabromobutyl group, a 5-fluoropentyl group, a 5-chloropentyl group, a 5-bromopentyl group, a 2,2,3,3,4,4,5,5-octafluoropentyl group ($-CH_2(CF_2)_4H$), a 2,2,3,3,4,4,5,5-octachloropentyl group ($-CH_2(CCl_2)_4H$), a 2,2,3,3,4,4,5,5-octabromopentyl group ($-CH_2(CBr_2)_4H$), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group (—(CH$_2$)$_2$ (CF$_2$)$_7$CF$_3$), a 3,3,4,4,5,5,6,6,7,7,8,8,9,9,10,10,10-heptadecachlorodecyl group (—(CH$_2$)$_2$ (CCl$_2$)$_7$CCl$_3$), a 3,3,4,4,5,5,6,6,7,7,8,8,9,9,10,10,10-heptadecabromodecyl group (—(CH$_2$)$_2$ (CBr$_2$)$_7$CBr$_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group, a perbromododecyl group, and the like. Among them, a perfluoroalkyl group having 1 to 6 carbon atoms is preferable, in particular, a trifluoromethyl group or a pentafluoroethyl group is more preferable.

The alkyl group exemplified as the substituent may be any of linear, branched or cyclic, and includes those having generally 1 to 12, preferably 1 to 6, and more preferably 1 to 3 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like. Among them, a methyl group is preferable.

The aryl group exemplified as the substituent includes those having generally 6 to 14 carbon atoms. Specifically, the aryl group includes phenyl group, naphthyl group, anthryl group, and the like.

The alkoxy group exemplified as the substituent may be any of linear, branched or cyclic, and includes those having generally 1 to 12, preferably 1 to 6, and more preferably 1 to 3 carbon atoms. Specifically, the alkoxy group includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a cyclopropoxy group, a cyclobutoxy group, a cyclopentyloxy group, a cyclohexyloxy group, a cycloheptyloxy group, a cyclooctyloxy group, a cyclononyloxy group, a cyclodecyloxy group, a cycloundecyloxy group, a cyclododecyloxy group, and the like. Among them, for example, a methoxy group, an ethoxy group, a n-propoxy group, and the like are preferable.

The acyl group exemplified as the substituent includes those having generally 2 to 20 carbon atoms derived from carboxylic acids. Specifically, the acyl group includes those derived from aliphatic carboxylic acids such as, for example, an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, a dodecanoyl group, a tridecanoyl group, a tetradecanoyl group, a pentadecanoyl group, a hexadecanoyl group, a heptadecanoyl group, an octadecanoyl group, a nonadecanoyl group, an icosanoyl group; and those derived from aromatic carboxylic acids such as, for example, a benzoyl group, a naphthoyl group.

In the general formula [25], the alkyl group represented by $R^7$ may be any of linear, branched or cyclic, and includes those having generally 1 to 12, preferably 1 to 6, and more preferably 1 to 3 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group. Among them, a methyl group is preferable.

The haloalkyl group represented by $R^7$ may be any of linear, branched or cyclic, and includes, for example, those in which a part or all of hydrogen atoms in the alkyl group having generally 1 to 12, preferably 1 to 6, and more preferably 1 to 3 carbon atoms are substituted by a halogen atom (for example, a fluorine atom, a chlorine atom, a bromine atom, an iodine atom, and the like are included, and a fluorine atom is particularly preferable). Specifically the haloalkyl group includes, for example, a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, a 2-bromoethyl group, a pentafluoroethyl group, a pentachloroethyl group, a pentabromoethyl group, a pentaiodoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonabromobutyl group, a 5-fluoropentyl group, a 5-chloropentyl group, a 5-bromopentyl group, a 2,2,3,3,4,4,5,5-octafluoropentyl group (—CH$_2$ (CF$_2$)$_4$H), a 2,2,3,3,4,4,5,5-octachloropentyl group (—CH$_2$ (CCl$_2$)$_4$H), a 2,2,3,3,4,4,5,5-octabromopentyl group (—CH$_2$ (CBr$_2$)$_4$H), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group (—(CH$_2$)$_2$(CF$_2$)$_7$CF$_3$), a 3,3,4,4,5,5,6,6,7,7,8,8,9,9,10,10,10-heptadecachlorodecyl group (—(CH$_2$)$_2$(CCl$_2$)$_7$CCl$_3$), a 3,3,4,4,5,5,6,6,7,7,8,8,9,9,10,10,10-heptadecabromodecyl group (—(CH$_2$)$_2$(CBr$_2$)$_7$CBr$_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group, a perbromododecyl group, and the like. Among them, a perfluoroalkyl group having 1 to 6 carbon atoms is preferable, in particular, a trifluoromethyl group, a pentafluoroethyl group and the like are more preferable.

The aryl group represented by R$^7$ includes those having generally 6 to 14 carbon atoms. Specifically, the aryl group includes a phenyl group, a naphthyl group, an anthryl group, and the like.

The aralkyl group represented by R$^7$ includes those having generally 7 to 15 carbon atoms. Specifically, the aralkyl group includes a benzyl group, a phenethyl group, a phenylpropyl group, a naphthylmethyl group, and the like.

In the general formula [9], m represents an integer of generally 1 to 6, and preferably 1 to 3. In addition, m pieces of X$_1$ may be the same or different from each other.

In the general formulas [4] and [5], the alkenyl group of the optionally substituted alkenyl group represented by R$^4$ and R$^5$ may be any of linear, branched or cyclic, and includes those having generally 2 to 12, and preferably 2 to 6. Specifically, the alkenyl group includes, for example, a vinyl group, an allyl group, a 1-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, a 2-methyl-2-butenyl group, a 1-hexenyl group, a 2-hexenyl group, a 3-hexenyl group, a 5-hexenyl group, a 2-methyl-2-pentenyl group, a 1-heptenyl group, a 2-heptenyl group, a 3-heptenyl group, a 4-heptenyl group, a 5-heptenyl group, a 6-heptenyl group, a 1-dodecenyl group, a 2-dodecenyl group, a 3-dodecenyl group, a 4-dodecenyl group, a 5-dodecenyl group, a 6-dodecenyl group, a 7-dodecenyl group, a 8-dodecenyl group, a 9-dodecenyl group, a 10-dodecenyl group, a 11-dodecenyl group, a 1-cyclobutenyl group, a 1-cyclopentenyl group, a 1-cyclohexenyl group, and the like.

The alkynyl group of the optionally substituted an alkynyl group represented by R$^4$ and R$^5$ may be any of linear, branched or cyclic, and includes those having generally 2 to 12, and preferably 2 to 6. Specifically, the alkynyl group includes, for example, an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-3-butynyl group, a 1-hexynyl group, a 2-hexynyl group, 3-hexynyl group, a 4-hexynyl group, a 5-hexynyl group, a 2-methyl-4-heptynyl group, a 1-heptynyl group, a 2-heptynyl group, a 3-heptynyl group, a 4-heptynyl group, a 5-heptynyl group, a 6-heptynyl group, a 1-octynyl group, a 2-octynyl group, 3-octynyl group, a 4-octynyl group, a 5-octynyl group, a 6-octynyl group, a 7-octynyl group, a 1-nonynyl group, a 2-nonynyl group, a 3-nonynyl group, a 4-nonynyl group, a 5-nonynyl group, a 6-nonynyl group, a 7-nonynyl group, a 8-nonynyl group, a 1-decynyl group, a 3-decynyl group, a 5-decynyl group, a 7-decynyl group, a 9-decynyl group, a 1-undecynyl group, a 3-undecynyl group, a 5-undecynyl group, a 7-undecynyl group, a 9-undecynyl group, a 1-dodecynyl group, a 3-dodecynyl group, a 5-dodecynyl group, a 7-dodecynyl group, a 9-dodecynyl group, a 11-dodecynyl group, and the like.

The aryl group of the optionally substituted aryl group represented by R$^4$ and R$^5$ includes those having generally 6 to 14, and preferably 6 to 10 carbon atoms. Specifically, the aryl group includes, for example, a phenyl group, a naphthyl group, a phenanthryl group, an anthryl group, and the like. Among them, a naphthyl group is preferable.

The heterocyclic group of the optionally substituted heterocyclic group represented by R$^4$ and R$^5$ includes, for example, 5-membered ring or 6-membered ring containing 1 to 3 hetero atoms such as a nitrogen atom, an oxygen atom, and a sulfur atom. Specifically, the heterocyclic group includes aliphatic heterocyclic groups such as, for example, a pyrrolidyl-2-on group, a piperidyl group, a piperidino group, a piperazinyl group and morpholino group; aromatic heterocyclic groups such as, for example, a pyridyl group, an imidazolyl group, a thiazolyl group, a furyl group and a pyranyl group; and the like.

The substituent of the optionally substituted, alkyl group, hetero-atom-containing alkyl group, alkenyl group, alkynyl group, aryl group or heterocyclic group, represented by R$^4$ and R$^5$ includes, for example, a group represented by the general formula [1], a halogen atom, an aryl group, an aralkyl group, an alkoxy group, an acyl group, an optionally substituted amino group, a cyano group, a nitro group, a hydroxyl group, a carboxyl group, a formyl group, a sulfo group, and the like.

The halogen atom exemplified as the substituent includes, for example, a fluorine atom, a chlorine atom, a bromine atom, an iodine atom, and the like. Among them, a fluorine atom is preferable.

The aryl group exemplified as the substituent includes those having generally 6 to 14 carbon atoms. Specifically, the aryl group includes a phenyl group, a naphthyl group, an anthryl group, and the like.

The aralkyl group exemplified as the substituent includes those having generally 7 to 12 carbon atoms. Specifically, the aralkyl group includes a benzyl group, a phenethyl group, a phenylpropyl group, a phenylbutyl group, a phenylpentyl group, a phenylhexyl group, and the like. Among them, a benzyl group is preferable.

The alkoxy group exemplified as the substituent may be any of linear, branched or cyclic, and includes those having generally 1 to 12, preferably 1 to 6, and more preferably 1 to 3 carbon atoms. Specifically, the alkoxy group includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a cyclopropoxy group, a cyclobutoxy group, a cyclopentyloxy group, a cyclohexyloxy group, a cycloheptyloxy group, a cyclooctyloxy group, a cyclononyloxy group, a cyclodecyloxy group, a cycloundecyloxy group, a cyclododecyloxy group, and the like. Among them, for example, a methoxy group, an ethoxy group, a n-propoxy group, and the like are preferable.

The acyl group exemplified as the substituent includes those derived from aliphatic carboxylic acids and aromatic carboxylic acids.

The acyl group derived from aliphatic carboxylic acids may be any of linear, branched or cyclic, and further may have a double bond in the chain, and includes those having generally 1 to 20, and preferably 1 to 15 carbon atoms. Specifically, the acyl group includes the acyl group derived from saturated aliphatic carboxylic acids such as, for example, a formyl group, an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, an undecanoyl group, a lauroyl group, a myristoyl group, a palmitoyl group, a stearoyl group, an icosanoyl group and a cyclohexylcarbonyl group; and the acyl group derived from unsaturated aliphatic carboxylic acids such as, for example, an acryloyl group, a methacryloyl group, a crotonoyl group and an oleoyl group.

The acyl group derived from aromatic carboxylic acids includes those having generally 7 to 15, and preferably 7 to 11 carbon atoms. Specifically, the acyl group includes, for example, a benzoyl group, a naphthoyl group, a toluoyl group, an anthoyl group, and the like.

The substituted amino group exemplified as the substituent includes those in which 1 to 2 hydrogen atoms of the amino group are substituted by a substituent such as, for example, an alkyl group having 1 to 6 carbon atoms, an alkenyl group, an alkynyl group, an aryl group, an aralkyl group, an acyl group, an oxycarbonyl group, a sulfonyl group, an alkylsylyl group.

The alkyl group having 1 to 6 carbon atoms exemplified as the substituent of the substituted amino group may be any of linear, branched or cyclic. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a cyclopropyl group, a cyclobutyl group, a cyclopentyl group, a cyclohexyl group, an adamantyl group, and the like.

The alkenyl group exemplified as the substituent of the substituted amino group may be any of linear, branched or cyclic, and includes those having generally 2 to 12, and preferably 2 to 6. Specifically, the alkenyl group includes, for example, a vinyl group, an allyl group, a 1-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, a 2-methyl-2-butenyl group, a 1-hexenyl group, a 2-hexenyl group, a 3-hexenyl group, a 5-hexenyl group, a 2-methyl-2-pentenyl group, a 1-heptenyl group, a 2-heptenyl group, a 3-heptenyl group, a 4-heptenyl group, a 5-heptenyl group, a 6-heptenyl group, a 1-dodecenyl group, a 2-dodecenyl group, a 3-dodecenyl group, a 4-dodecenyl group, a 5-dodecenyl group, a 6-dodecenyl group, a 7-dodecenyl group, a 8-dodecenyl group, a 9-dodecenyl group, a 10-dodecenyl group, a 11-dodecenyl group, a 1-cyclobutenyl group, a 1-cyclopentenyl group, a 1-cyclohexenyl group, and the like.

The alkynyl group exemplified as the substituent of the substituted amino group may be any of linear, branched or cyclic, and includes those having generally 2 to 12, and preferably 2 to 6. Specifically, the alkynyl group includes, for example, an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-3-butynyl group, a 1-hexynyl group, a 2-hexynyl group, a 3-hexynyl group, a 4-hexynyl group, a 5-hexynyl group, a 2-methyl-4-heptynyl group, a 1-heptynyl group, a 2-heptynyl group, a 3-heptynyl group, a 4-heptynyl group, a 5-heptynyl group, a 6-heptynyl group, a 1-octynyl group, a 2-octynyl group, a 3-octynyl group, a 4-octynyl group, a 5-octynyl group, a 6-octynyl group, a 7-octynyl group, a 1-nonynyl group, a 2-nonynyl group, a 3-nonynyl group, a 4-nonynyl group, a 5-nonynyl group, a 6-nonynyl group, a 7-nonynyl group, a 8-nonynyl group, a 1-decynyl group, a 3-decynyl group, a 5-decynyl group, a 7-decynyl group, a 9-decynyl group, a 1-undecynyl group, a 3-undecynyl group, a 5-undecynyl group, a 7-undecynyl group, a 9-undecynyl group, a 1-dodecynyl group, a 3-dodecynyl group, a 5-dodecynyl group, a 7-dodecynyl group, a 9-dodecynyl group, a 11-dodecynyl group, and the like.

The aryl group exemplified as the substituent of the substituted amino group includes those having generally 6 to 14, and preferably 6 to 10 carbon atoms. Specifically, the aryl group includes, for example, a phenyl group, a naphthyl group, a phenanthryl group, an anthryl group, and the like. Among them, a phenyl group is preferable.

The aralkyl group exemplified as the substituent of the substituted amino group includes those having generally 7 to 12. Specifically, the aralkyl group includes, for example, a benzyl group, a phenethyl group, a phenylpropyl group, a phenylbutyl group, a phenylpentyl group, a phenylhexyl group, and the like. Among them, a benzyl group is preferable.

The acyl group exemplified as the substituent of the substituted amino group includes, for example, those derived from aliphatic carboxylic acids, aromatic carboxylic acids, and aromatic-aliphatic carboxylic acids, and the like.

The acyl group derived from aliphatic carboxylic acids may be any of linear, branched or cyclic, and further may have a double bond in the chain, and includes those having generally 1 to 20, and preferably 1 to 15 carbon atoms. Specifically, the acyl group includes the acyl group derived from saturated aliphatic carboxylic acids such as, for example, a formyl group, an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, an undecanoyl group, a lauroyl group, a myristoyl group, a palmitoyl group, a stearoyl group, an icosanoyl group and cyclohexylcarbonyl group; the halogenated acyl groups such as, for example, a chloroacetyl group, a trichloroacetyl group, a trifluoroacetyl group and a chlorobutanoyl group; and the acyl group derived from unsaturated aliphatic carboxylic acids such as, for example, an acryloyl group, a methacryloyl group, a crotonoyl group and an oleoyl group; and the like.

The acyl group derived from aromatic carboxylic acids includes those having generally 7 to 15, and preferably 7 to 11 carbon atoms. Specifically, the acyl group includes, for example, a benzoyl group, a nitrobenzoyl group, a p-phenylbenzoyl group, a naphthoyl group, a toluoyl group, an anthoyl group, and the like.

The acyl group derived from aromatic aliphatic carboxylic acids includes those having generally 8 to 16 carbon atoms. Specifically, the acyl group includes, for example, a phenylacetyl group, a nitrophenylacetyl group, a phenylpropionyl group, a nitrophenylpropionyl group, and the like.

The oxycarbonyl group exemplified as the substituent of the substituted amino group includes an alkoxycarbonyl group having 1 to 4 carbon atoms such as, for example, a methoxycarbonyl group, an ethoxycarbonyl group, a tert-butoxycarbonyl group and 2,2,2-trichloroethoxycarbonyl group; an aralkyloxycarbonyl group such as, for example, a benzyloxycarbonyl group and a 4-methoxybenzyloxycarbonyl group; for example, a 9-fluorenylmethyloxycarbonyl group, an allyloxycarbonyl group, and the like.

The sulfonyl group exemplified as the substituent of the substituted amino group includes an alkyl sulfonyl group having 1 to 4 carbon atoms such as, for example, a methanesulfonyl group, an ethanesulfonyl group, a propanesulfonyl group, a butanesulfonyl group and an tert-butanesulfonyl group; an arylsulfonyl group such as, for example, a p-toluenesulfonyl group and a benzenesulfonyl group; and the like.

The alkylsilyl group exemplified as the substituent of the substituted amino group includes those in which a part or all of hydrogen atoms of the silyl group are substituted by an alkyl group having 1 to 6, and preferably 1 to 4 carbon atoms, and said alkyl group may be any of linear, branched or cyclic. Specifically, the alkylsylyl group includes, for example, a methylsilyl group, an ethylsilyl group, a n-propylsilyl group, an isopropylsilyl group, a n-butylsilyl group, an isobutylsilyl group, a sec-butylsilyl group, a tert-butylsilyl group, a neobutylsilyl group, a n-pentylsilyl group, an isopentylsilyl group, a sec-pentylsilyl group, a tert-pentylsilyl group, a neopentylsilyl group, a n-hexylsilyl group, an isohexylsilyl group, a sec-hexylsilyl group, a tert-hexylsilyl group, a neohexylsilyl group, a cyclopropylsilyl group, a cyclobutylsilyl group, a cyclopentylsilyl group, a cyclohexylsilyl group, a dimethylsilyl group, a diethylsilyl group, a di-n-propylsilyl group, a diisopropylsilyl group, a di-n-butylsilyl group, a diisobutylsilyl group, a di-sec-butylsilyl group, a di-tert-butylsilyl group, a dineobutylsilyl group, a di-n-pentylsilyl group, a diisopentylsilyl group, a di-sec-pentylsilyl group, a di-tert-pentylsilyl group, a dineopentylsilyl group, a di-n-hexylsilyl group, a diisohexylsyiyl group, a di-sec-hexylsilyl group, a di-tert-hexylsilyl group, a dineohexylsilyl group, a dicyclopropylsilyl group, a dicyclobutylsilyl group, a dicyclopentylsilyl group, a dicyclohexylsilyl group, a trimethylsilyl group, a triethylsilyl group, a tri-n-propylsilyl group, a triisopropylsilyl group, a tri-n-butylsilyl group, a triisobutylsilyl group, a tri-sec-butylsilyl group, a tri-tert-butylsilyl group, a trineobutylsilyl group, a tri-n-pentylsilyl group, a triisopentylsilyl group, a tri-sec-pentylsilyl group, a tri-tert-pentylsilyl group, a trineopentylsilyl group, a tri-n-hexylsilyl group, a triisohexylsilyl group, a tri-sec-hexylsilyl group, a tri-tert-hexylsilyl group, a trineohexylsilyl group, a tricyclopropylsilyl group, a tricyclobutylsilyl group, a tricyclopentylsilyl group, a tricyclohexylsilyl group, a dimethylethylsilyl group, a tert-butyldimethylsilyl group, a dimethylisopropylsilyl group, a diethylisopropylsilyl group, a pentyldimethylsilyl group, a hexyldimethylsilyl group, and the like.

Preferable specific examples of the substituted amino group include an alkyl-substituted amino group such as, for example, a methylamino group, a dimethylamino group, an ethylamino group, a tert-butylamino group and an adamantylamino group; an alkenyl-substituted amino group such as, for example, a vinylamino group and an allylamino group; an alkyl-substituted amido group such as, for example, a formamide group, an acetamide group, a chloroacetamide group, a trichloroacetamide group, a trifluoroacetamide group, a nitrophenylacetamide group, a nitrophenoxyacetamide group, a propaneamide group and chlorobutaneamide group; an aryl-substituted amide group such as, for example, a benzamide group, a nitrobenzamide group and a p-phenylbenzamide group; an aralkyl-substituted amide group such as, for example, a phenylacetamide group, a phenylpropanamide group and a nitrophenylpropaneamide group; an acyl-substituted amide group such as, for example, an acrylamide group, a methacrylamide group, a trimethylsilylamide group and a tert-butyldimethylsilylamide group; an oxycarbonyl-substituted amino group (a carbamate group) such as, for example, a tert-butoxycarbonyl group, a benzyloxycarbonyl group, a 4-methoxybenzyloxycarbonyl group and a 9-fluorenylmethyloxycarbonyl group; a sulfonyl-substituted amino group (a sulfonamide group) such as, for example, a methanesulfonamide group, a trifluoromethanesulfonamide group, a benzenesulfonamide group, a naphthalenesulfonamide group, an anthracenesulfonamide group, a p-toluenesulfonamide group and a p-methoxyphenylsulfonamide group; an alkylsilyl-substituted amino group such as, for example, a trimethylsilylamino group, a triisopropylsylylamino group and a tert-butyldimethylsilyl group; and the like.

In the general formulas [4] and [5], preferable specific examples of the substituted aryl group represented by $R^4$ and $R^5$ include an alkyl-substituted aryl group such as, for example, a tolyl group and a xylyl group; an amino-substituted aryl group such as, for example, an aminophenyl group and an aminonaphthyl group; an acylamino-substituted aryl group such as, for example, a benzylaminophenyl group, a phenoxycarbonylaminophenyl group, a benzamidephenyl group, an acrylaminophenyl group and a methacrylaminophenyl group; and the like.

In the general formulas [6] to [8], the substituted or unsubstituted alkylene chain which may have a hetero atom in the chain, represented by $T_1$ to $T_3$ includes those in which the optionally substituted alkylene chain has generally 0 to 6, and preferably 0 to 4 hetero atoms. Specifically, the alkylene chain includes those represented by the general formula [10]:

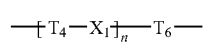

$$-\!\!\!-\!\!\!\left[T_4\!-\!X_1\right]_{\overline{n}}\!\!\!-\!T_6\!-\!\!\!-$$ [10]

(wherein, $T_6$ represents an optionally substituted alkylene chain having 1 to 8 carbon atoms, n represents an integer of 0 to 6, and $T_4$ and $X_1$ are same as the above).

In the general formulas [6] to [8] and [10], the alkylene chain of the optionally substituted alkylene chain having 1 to 8 carbon atoms, represented by $T_1$ to $T_3$ and $T_6$ includes a linear alkyl group having generally 1 to 8, and preferably 1 to 5. Specifically, the alkylene chain includes, for example, a methylene group, an ethylene group, a trimethylene group, a tetramethylene group, a pentamethylene group, a hexamethylene group, a heptamethylene group, an octamethylene group, and the like.

In the general formula [6], the substituted or unsubstituted arylene chain represented by $T_1$ includes those having generally 6 to 14, and preferably 6 to 10 carbon atoms. Specifically, the arylene chain includes, for example, a phenylene group, a naphthylene group, and the like.

In the general formula [8], the alkenylene chain of the substituted or unsubstituted alkenylene chain represented by $T_1$ includes those having generally 1 to 6, and preferably one carbon-carbon double bond in the chain and also having generally 2 to 12 carbon atoms. Specifically, the alkenylene chain includes, for example, a vinylene group, a propenylene group, an isopropenylene group, a 1-butenylene group, a 2-butenylene group, a 1-pentenylene group, a 2-pentenylene group, a 1-hexenylene group, a 2-hexenylene group, a 3-hexenylene group, a 1-heptenylene group, a 2-heptenylene group, a 3-heptenylene group, a 1-octenylene group, a 2-octenylene group, a 3-octenylene group, a 4-octenylene group, a 1-nonenylene group, a 2-nonenylene group, a 3-nonenylene group, a 4-nonenylene group, a 1-dodecenylene group, a 2-dodecenylene group, a 3-dodecenylene group, a 4-dodecenylene group, a 5-dodecenylene group, a 1-undecenylene group, a 2-undecenylene group, a 3-undecenylene group, a 4-undecenylene group, a 5-undecenylene group, a 1-dodecenylene group, a 2-dodecenylene group, a 3-dodecenylene group, a 4-dodecenylene group, a 5-dodecenylene group, a 6-dodecenylene group, and the like.

In the general formulas [6] to [8] and [10], the substituent of the optionally substituted alkylene chain having 1 to 8 carbon atoms, represented by $T_1$ to $T_3$ and $T_6$, the substituent of the substituted alkenylene chain represented by $T_3$, and the substituent of the substituted arylene chain represented by $T_1$ include, for example, a group represented by the above general formula [1], a halogen atom, a haloalkyl group, an alkyl group, an aryl group, a cyano group, a nitro group, a hydroxyl group, a carboxyl group, a formyl group, a sulfo group, and the like.

The halogen atom exemplified as the substituent includes, for example, a fluorine atom, a chlorine atom, a bromine atom, an iodine atom, and the like.

The haloalkyl group exemplified as the substituent may be any of linear, branched or cyclic, and includes, for example, those in which a part or all of hydrogen atoms in the alkyl group having generally 1 to 12, preferably 1 to 6, and more preferably 1 to 3 carbon atoms are substituted by a halogen atom (for example, a fluorine atom, a chlorine atom, a bromine atom, an iodine atom, and the like are included, and a fluorine atom is particularly preferable). Specifically, the haloalkyl group includes, for example, a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, a 2-bromoethyl group, a pentafluoroethyl group, a pentachloroethyl group, a pentabromoethyl group, a pentaiodoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonabromobutyl group, a 5-fluoropentyl group, a 5-chloropentyl group, a 5-bromopentyl group, a 2,2,3,3,4,4,5,5-octafluoropentyl group (—$CH_2(CF_2)_4H$), a 2,2,3,3,4,4,5,5-octachloropentyl group (—$CH_2(CCl_2)_4H$), a 2,2,3,3,4,4,5,5-octabromopentyl group (—$CH_2(CBr_2)_4H$), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group (—$(CH_2)_2(CF_2)_7CF_3$), a 3,3,4,4,5,5,6,6,7,7,8,8,9,9,10,10,10-heptadecachlorodecyl group (—$(CH_2)_2(CCl_2)_7CCl_3$), a 3,3,4,4,5,5,6,6,7,7,8,8,9,9,10,10,10-heptadecabromodecyl group (—$(CH_2)_2(CBr_2)_7CBr_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group, a perbromododecyl group, and the like. Among them, a perfluoroalkyl group having 1 to 6 carbon atoms is preferable, in particular, for example, a trifluoromethyl group, a pentafluoroethyl group, and the like are more preferable.

The alkyl group exemplified as the substituent may be any of linear, branched or cyclic, and includes those having generally 1 to 12, preferably 1 to 6, and more preferably 1 to 3 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like. Among them, a methyl group, an ethyl group, a n-propyl group, an isopropyl group, and the like are preferable.

The aryl group exemplified as the substituent includes those having generally 6 to 14. Specifically, the aryl group includes, for example, a phenyl group, a naphthyl group, an anthryl group, and the like.

In the general formula [10], n is generally 0 to 6, preferably 0 to 4, and more preferably 0 to 2.

Among $T_1$ and $T_2$ in the general formulas [6] and [7], a substituted or unsubstituted alkylene chain is preferable, in particular an unsubstituted alkylene chain is more preferable.

Among $T_3$ in the general formulas [8], a substituted or unsubstituted alkenylene chain is preferable, in particular, an unsubstituted or alkyl-substituted alkenylene chain is more preferable.

The corresponding sulfonate ester compound obtained by reacting (a) a compound having a sulfo group with (b) a compound having a group represented by the general formula [1] includes, for example, the following compounds.

Namely, (i) a compound represented by the general formula [11]:

$$R^4\text{—}SO_2\text{—}OR^5 \qquad [11]$$

(wherein, $R^4$ and $R^5$ are same as the above) obtained by reacting (a) 1 equivalent of sulfonic acid represented by the general formula [4] with (b) 1 equivalent of a compound represented by the general formula [5];

(ii) a compound represented by the general formula [12]:

$$R^5O\text{—}SO_2\text{-}T_1\text{-}SO_2\text{—}OR^5 \qquad [12]$$

(wherein, $R^5$ and $T_1$ are same as the above) obtained by reacting (a) 2 equivalents or more of disulfonic acid represented by the general formula [6] with (b) 1 equivalent of a compound represented by the general formula [5]; or a compound represented by the general formula [13]:

$$HO_3S\text{-}T_1\text{-}SO_2\text{—}OR^5 \qquad [13]$$

(wherein, $R^5$ and $T_1$ are same as the above) obtained by reacting (a) 1 equivalent of said disulfonic acid with (b) 1 equivalent of a compound represented by the general formula [5];

(iii) a compound represented by the general formula [14]:

$$R^4\text{—}SO_2\text{—}O\text{-}T_2\text{-}OR^1 \quad [14]$$

(wherein, $T_2$ is same as the above) obtained by reacting (a) 2 equivalents of sulfonic acid represented by the general formula [4] with (b) 1 equivalent of a compound represented by the general formula [7]; or a compound represented by the general formula [15]:

$$R^4\text{—}SO_2\text{—}O\text{-}T_2\text{-}O\text{—}SO_2\text{—}R^4 \quad [15]$$

(wherein, $R^1$ and $T_2$ are same as the above) obtained by reacting (a) 1 equivalent of said sulfonic acid with (b) 1 equivalent of a compound represented by the general formula [7];

(iv) a cyclic disulfonate ester represented by the general formula [16]:

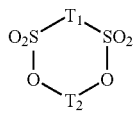

[16]

(wherein, $T_1$ and $T_2$ are same as the above) obtained by reacting (a) 1 equivalent of disulfonic acid represented by the general formula [6] with (b) 1 equivalent of a compound represented by the general formula [7];

(v) a compound represented by the general formula [17]:

[17]

(wherein, $T_3$ is same as the above) obtained from a compound of the general formula [8] which corresponds to a compound in the case that (a) and (b) are the same compound; and the like.

Representative specific examples of the compound represented by the general formula [11] include an unsaturated aliphatic sulfonate ester such as, for example, methyl vinylsulfonate and methyl allylsulfonate; a substituted arylsulfonate such as, for example, methyl toluenesulfonate, methyl xylenesulfonate, methyl aminobenzenesulfonate, methyl benzoylaminobenzenesulfonate and methyl aminonaphthalenesulfonate; a substituted aminobenzenesulfonate such as, for example, methyl acrylamidebenzenesulfonate, methyl methacrylamidebenzenesulfonate and methyl methylaminobenzenesulfonate; and the like.

Representative specific examples of the compound represented by the general formula [12] include a saturated aliphatic sulfonate diester such as, for example, dimethyl methanedisulfonate, diethyl methanedisulfonate, dimethyl ethanedisulfonate and diethyl ethanedisulfonate; an arylsulfonate diester such as, for example, dimethyl benzene-1,2-disulfonate, dimethyl benzene-1,3-disulfonate and dimethyl benzene-1,4-disulfonate; a substituted arylsulfonate diester such as, for example, dimethyl 1-vinylbenzene-3,5-disulfonate, dimethyl 1-acrylamidebenzene-3,5-disulfonate and dimethyl 1-methacrylamidebenzene-3,5-disulfonate; and the like.

Representative specific examples of the compound represented by the general formula [13] include a saturated aliphatic sulfonate monoester such as, for example, methanedisulfonate monomethyl ester, methanedisulfonate monoethyl ester, ethanedisulfonate monomethyl ester and ethanedisulfonate monoethyl ester; an arylsulfonate monoester such as, for example, benzene-1,2-disulfonate monomethyl ester, benzene-1,3-disulfonate monomethyl ester and benzene-1,4-disulfonate monomethyl ester; a substituted arylsulfonate monoester such as, for example, 1-vinylbenzene-3,5-disulfonate monomethyl ester, 1-acrylamidebenzene-3,5-disulfonate monomethyl ester and 1-methacrylamidebenzene-3,5-disulfonate monomethyl ester; and the like.

Representative specific examples of the compound represented by the general formula [14] include, for example, vinylsulfonyloxymethylenemesylate, allylsulfonyloxymethylenemesylate, benzenesulfonyloxymethylenemesylate, 1-(vinylsulfonyloxy)ethylene-2-tosylate, 1-(allylsulfonyloxy)ethylene-2-tosylate, 1-(benzenesulfonyloxy)ethylene-2-tosylate, 1-(p-toluenesulfonyloxy)ethylene-2-triflate, and the like.

Representative specific examples of the compound represented by the general formula [15] include, for example, methylene-bis(vinylsulfonate), methylene-bis(allylsulfonate), methylene-bis(vinylbenzenesulfonate), 1,2-ethylene-bis(benzoylaminobenzenesulfonate), and the like.

Representative specific examples of the compound represented by the general formula [16] include, for example, tetramethylenemethane disulfonate, trimethylenemethane disulfonate, ethylenemethane disulfonate, methylenemethane disulfonate, pentamethylenemethane disulfonate, pentamethylene 1,1-ethanedisulfonate, tetramethylene 1,1-ethanedisulfonate, trimethylene 1,1-ethanedisulfonate, ethylene 1,1-ethanedisulfonate, and the like.

Representative specific examples of the compound represented by the general formula [17] include, for example, propanesultone, butanesultone, pentanesultone, hexanesultone, and the like.

The organic base includes those which can form a salt with (a) a compound having a sulfa group. Specifically, the organic base includes, for example, a secondary amine, a tertiary amine or a quaternary ammonium salt.

The secondary amine and the tertiary amine include, for example, those represented by the general formula [18]:

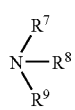

[18]

(wherein, $R^7$ to $R^9$ each independently represent a hydrogen atom or an alkyl group, and $R^7$ to $R^9$ together with a nitrogen atom to which these groups bind may form a hetero ring, excepting the case when two or all of $R^7$ to $R^9$ are hydrogen atoms).

The quaternary ammonium salt includes, for example, those represented by the general formula [19]:

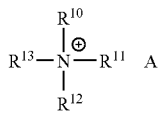

[19]

(wherein, $R^{10}$ to $R^{13}$ each independently represent an alkyl group or an aralkyl group, and A represents a counter anion. Further, three of $R^{10}$ to $R^{13}$ together with a nitrogen atom to which these groups bind may form a hetero ring), and the like.

Specific example of the case when three of $R^{10}$ to $R^{13}$ in the general formula [19] together with a nitrogen atom to which these groups bind form a hetero ring in the cation part of said quaternary ammonium salt includes, for example, an imidazolium ion represented by the general formula [20]:

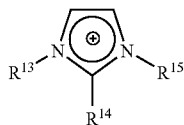

[20]

(wherein, $R^{14}$ represents a hydrogen atom, an alkyl group or an aralkyl group, $R^{15}$ represents an alkyl group or an aralkyl group, and $R^{13}$ is same to the above), a pyridinium ion represented by the general formula [21]:

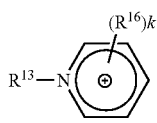

[21]

(wherein, k pieces of $R^{16}$ each independently represent an alkyl group, k represents an integer of 0 to 5, and $R^{13}$ is same to the above), and a bipyridinium ion represented by the general formula [22]:

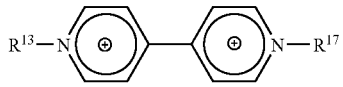

[22]

(wherein, $R^{17}$ represents an alkyl group or an aralkyl group, and $R^{13}$ is same to the above), and the like. Among them, a pyridinium ion represented by the general formula [21] is preferable.

In the general formulas [18] to [22], the alkyl group represented by $R^7$ to $R^{17}$ may be any of linear, branched or cyclic, and includes those having generally 1 to 12, and preferably 1 to 4 carbon atoms. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, an neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like. Among them, for example, a methyl group, an ethyl group, a n-propyl group, an isopropyl group, a n-butyl group, and the like are preferable.

In the general formulas [19] and [20], the aralkyl group represented by $R^{10}$ to $R^{15}$ includes those having generally 7 to 15 carbon atoms. Specifically, the aralkyl group includes, for example, a benzyl group, a phenethyl group, a 1-phenylethyl group, a 2-phenylpropyl group, a 3-phenylpropyl group, a phenylbutyl group, a 1-methyl-3-phenylpropyl group, a naphthylmethyl group, and the like.

The hetero ring formed by $R^7$ to $R^9$ together with a nitrogen atom to which these groups bind in the general formula [18] and the hetero ring formed by three of $R^{10}$ to $R^{13}$ together with a nitrogen atom to which these groups bind in the general formula [19] are, for example, 5-membered or 6-membered ring, and may contain 1 to 2 hetero atoms (for example, a nitrogen atom, an oxygen atom, a sulfur atom, and the like) in addition to one nitrogen atom. Specifically, the hetero ring includes an aliphatic hetero ring such as, for example, a 2H-pyrrole ring, an imidazoline ring, a pyrazoline ring, a pyrroline ring, a piperidine ring, a piperazine ring, a morpholine ring and a thiazoline ring; an aromatic hetero ring such as, for example, a pyridine ring, an imidazole ring, a pyrazole ring, a thiazole ring, a furan ring, a pyran ring, a pyrrole ring, a pyrrolidine ring, a quinoline ring, an indole ring, an isoindoline ring, a carbazole ring; and the like.

Said aromatic hetero ring may further have a substituent of an alkyl group having 1 to 4 carbon atoms such as, for example, a methyl group, an ethyl group, a n-propyl group, an isopropyl group, a n-butyl group, a sec-butyl group, a tert-butyl group. Specific examples of such an aromatic hetero ring having a substituent include, for example, 2-picoline, 3-picoline, 4-picoline, 2,3-lutidine, 2,4-lutidine, 2,5-lutidine, 2,6-lutidine, α-collidine, β-collidine, γ-collidine, 2-isobutylpyridine, 2,6-di-tert-pyridine, 3-isobutylpyridine, 2-isopropylpyridine, 2-ethyl-6-isopropylpyridine, 2-n-propylpyridine, and the like.

Among the organic bases, tertiary amine is preferable, in particular, for example, pyridine, lutidine, collidine, and the like are more preferable.

Preferable specific examples of the secondary amine represented by the general formula [18] include secondary alkylamines such as, for example, dimethylamine, diethylamine, di-n-propylamine, diisopropylamine, di-n-butylamine, diisobutylamine, di-sec-butylamine, di-tert-butylamine, di-n-pentylamine, diisopentylamine, di-sec-pentylamine, di-tert-pentylamine, dineopentylamine, dihexylamine, diisohexylamine, di-sec-hexylamine, di-tert-hexylamine, dineohexylamine, diheptylamine, dioctylamine, bis(2-ethylhexyl)amine, didecylamine, dicetylamine, dicyclopropylamine, dicyclobutylamine, dicyclopentylamine, dicyclohexylamine, methylethylamine and isopropylethylamine; secondary arylamines such as, for example, diphenylamine, dinaphthylamine; secondary aralkylamines such as, for example, dibenzylamine; and secondary cyclic amines such as, for example, morpholine, piperidine, pyrrolidine and piperazine; and the like. Among them, secondary arylamines are preferable, and diphenylamine is more preferable.

Preferable specific examples of the tertiary amine represented by the general formula [18] include tertiary alkylamines such as, for example, trimethylamine, triethylamine, tri-n-propylamine, triisopropyl amine, tri-n-butylamine, tri-isobutylamine, tri-sec-butylamine, tri-tert-butylamine, tri-n-pentylamine, toriisopentylamine, tri-sec-pentylamine, tri-tert-pentylamine, trineopentylamine, trihexylamine, triisohexylamine, tri-sec-hexylamine, tri-tert-hexylamine, trineohexylamine, tricyclopropylamine, tricyclobutylamine, tricyclopentylamine, tricyclohexylamine, dimethylethylamine and diisopropylethylamine; tertiary arylamines such as, for example, triphenylamine and trinaphthylamine; tertiary aralkylamines such as, for example, tribenzylamine; and tertiary cyclic amines such as, for example, pyridine, 2,3-lutidine, 2,4-lutidine, 2,5-lutidine, 2,6-lutidine, 3,4-lutidine, 3,5-lutidine, 2,4,6-collidine, α-collidine (4-ethyl-2-methylpyridine), 3-collidine (3-ethyl-4-methylpyridine) and γ-collidine (2,4,6-collidine). Among them, tertiary cyclic amines are preferable, and pyridine, in particular, pyridine, lutidine and collidine are preferable.

Preferable specific examples of the cation part of the quaternary ammonium salt represented by the general formula [19] include a tetraalkylammonium ion such as, for example, tetraethylammonium ion, tetra-n-propylammonium ion, tetra-n-butylammonium ion, tetra-n-pentylammonium ion, tetra-n-hexylammonium ion, tetra-n-heptylammonium ion, tetra-n-octylammonium ion, tetra-n-nonylammonium ion, tetra-n-decylammonium ion, tetra-n-undecylammonium ion, tetralauryl(dodecyl)ammonium ion, tetra-n-tetradecylammonium ion, tetramyristyl(tetradecyl)ammonium ion, tetra-n-pentadecylammonium ion, tetracetylammonium ion, tetra-n-heptadecylammonium ion, trioctadecylmethylammonium ion, tridecylmethylammonium ion, trinonylmethylammonium ion, trioctylethylammonium ion, triheptylpentylammonium ion, triheptylpropylammonium ion, triheptylmethylammonium ion, trihexylbutylammonium ion, trihexylethylammonium ion, nonyltripentylammonium ion, hexyltripentylammonium ion, tripentylbutylammonium ion, tripentylmethylammonium ion, octyltributylammonium ion, hexyltributylammonium ion, decyltripropylammonium ion, undecyltripropylammonium ion, heptyltripropylammonium ion, hexyltripropylammonium ion, tripropylmethylammonium ion, decyltriethylammonium ion, octyltriethylammonium ion, octadecyltrimethylammonium ion, heptadecyltrimethylammonium ion, hexadecyltrimethylammonium ion, dodecyltrimethylammonium ion, decyltrimethylammonium ion, nonyltrimethylammonium ion, octyltrimethylammonium ion, hexyltrimethylammonium ion, ethyltrimethylammonium ion, undecylbutyldipropylammonium ion, undecylbutyldiethylammonium ion, undecylpropyldiethylammonium ion, nonyloctyldiethylammonium ion, nonyloctyldimethylammonium ion, nonylhexyldibutylammonium ion, nonylhexyldimethylammonium ion, nonylpentyldimethylammonium ion, nonylbutyldimethylammonium ion, octylhexyldipentylammonium ion, octylhexyldipropylammonium ion, octylhexyldimethylammonium ion, octylpentyldibutylammonium ion, octylpentyldipropylammonium ion, octylpentyldimethylammonium ion, octylbutyldipropylammonium ion, octylethyldimethylammonium ion, heptylpentyldimethylammonium ion, hexylpentyldibutylammonium ion, hexylpentyldimethylammonium ion, hexylbutyldimethylammonium ion and pentylbutyldipropylammonium ion; an aralkyltrialkylammonium ion such as, for example, benzyltrimethylammonium ion, benzyltriethylammonium ion, benzyltripropylammonium ion and benzyltri-n-propylammonium ion; and the like.

Preferable specific examples of the imidazolium ion represented by the general formula [20] include an alkyl-substituted imidazolium ion such as, for example, 1,3-dimethylimidazolium ion, 1-methyl-3-ethylimidazolium ion, 1-methyl-3-butylimidazoliumion, 1-methyl-3-pentylimidazolium ion, 1-methyl-3-hexylimidazolium ion, 1-methyl-3-octylimidazolium ion, 1-methyl-3-decylimidazolium ion, 1-methyl-3-dodecylimidazolium ion, 1-methyl-3-tetradecylimidazolium ion, 1-methyl-3-hexadecylimidazolium ion, 1-methyl-3-octadecylimidazolium ion, 1,3-diethylimidazolium ion, 1-ethyl-3-butylimidazolium ion, 1-ethyl-3-pentylimidazolium ion, 1-ethyl-3-hexylimidazolium ion, 1-ethyl-3-octylimidazolium ion, 1-ethyl-3-decylimidazolium ion, 1-ethyl-3-dodecylimidazolium ion, 1-ethyl-3-tetradecylimidazolium ion, 1-ethyl-3-hexadecylimidazolium ion and 1-ethyl-3-octadecylimidazolium ion; an aralkyl-substituted imidazolium ion such as, for example, 1-methyl-3-benzylimidazolium ion an 1-methyl-3-phenylpropylimidazolium ion; and a trialkyl-substituted imidazolium ion such as, for example, 1,2,3-trimethylimidazolium ion, 1,2-dimethyl-3-ethylimidazolium ion, 1,2-dimethyl-3-butylimidazolium ion, 1,2-dimethyl-3-propylimidazolium ion, 1,2-dimethyl-3-hexylimidazolium ion and 1,2-dimethyl-3-hexadecylimidazolium ion; and the like.

Preferable specific examples of the pyridinium ion represented by the general formula [21] include, for example, 1-methylpyridinium ion, 1-ethylpyridinium ion, 1,3-dimethylpyridinium ion, 1-methyl-3-ethylpyridinium ion, 1,3,5-trimethylpyridinium ion, 1-methyl-3,5-diethylpyridinium ion, and the like. Among them, for example, 1-methylpyridinium ion, and the like are preferable.

Preferable specific examples of the bipyridinium ion represented by the general formula [22] include a N,N'-dialkyl-4,4'-bipyridinium ion such as, for example, 1,1'-dimethyl-4,4'-bipyridinium ion, 1,1'-diethyl-4,4'-bipyridinium ion, 1,1'-dipropyl-4,4'-bipyridinium ion, 1,1'-dibutyl-4,4'-bipyridinium ion, 1,1'-dipentyl-4,4'-bipyridinium ion, 1,1'-dihexyl-4,4'-bipyridinium ion, 1,1'-diheptyl-4,4'-bipyridinium ion, 1,1'-dioctyl-4,4'-bipyridinium ion, 1,1'-dinonyl-4,4'-bipyridinium ion, 1,1'-didecyl-4,4'-bipyridinium ion, 1,1'-diundecyl-4,4'-bipyridinium ion, 1,1'-didodecyl-4,4'-bipyridinium ion, 1,1'-ditridecyl-4,4'-bipyridinium ion, 1,1'-ditetradecyl-4,4'-bipyridinium ion, 1,1'-dipentadecyl-4,4'-bipyridinium ion, 1,1'-dihexadecyl-4,4'-bipyridinium ion, 1,1'-diheptadecyl-4,4'-bipyridinium ion, 1,1'-dioctadecyl-4,4'-bipyridinium ion, 1,1'-dinonadecyl-4,4'-bipyridinium ion, 1,1'-diicosyl-4,4'-bipyridinium ion, 1-methyl-1'-ethyl-4,4'-bipyridinium ion, 1-methyl-1'-propyl-4,4'-bipyridinium ion, 1-methyl-1'-butyl-4,4'-bipyridinium ion, 1-methyl-1'-pentyl-4,4'-bipyridinium ion, 1-methyl-1'-hexyl-4,4'-bipyridinium ion, 1-methyl-1'-heptyl-4,4'-bipyridinium ion, 1-methyl-1'-octyl-4,4'-bipyridinium ion, 1-methyl-1'-nonyl-4,4'-bipyridinium ion, 1-methyl-1'-decyl-4,4'-bipyridinium ion, 1-methyl-1'-undecyl-4,4'-bipyridinium ion, 1-methyl-1'-dodecyl-4,4'-bipyridinium ion, 1-ethyl-1'-propyl-4,4'-bipyridinium ion, 1-ethyl-1'-butyl-4,4'-bipyridinium ion, 1-ethyl-1'-pentyl-4,4'-bipyridinium ion, 1-ethyl-1'-hexyl-4,4'-bipyridinium ion, 1-ethyl-1'-heptyl-4,4'-bipyridinium ion, 1-ethyl-1'-octyl-4,4'-bipyridinium ion, 1-ethyl-1'-nonyl-4,4'-bipyridinium ion, 1-ethyl-1'-decyl-4,4'-bipyridinium ion, 1-ethyl-1'-undecyl-4,4'-bipyridinium ion and 1-ethyl-1'-dodecyl-4,4'-bipyridinium ion; a N-alkyl-N'-aralkyl-4,4'-bipyridinium ion such as, for example, 1-methyl-1'-benzyl-4,4'-bipyridinium ion; and the like.

Preferable specific examples of the counter anion of the quaternary ammonium salt represented by the general formula [19] include inorganic-acid-derived ions such as, a halide ion including, for example, iodide ion, bromide ion, chloride ion; a halogen acid ion including, for example, iodate ion, bromated ion, chlorate ion; a perhalogen acid ion including, for example, periodate ion, perbromate ion, perchlorate ion; a halous acid ion including, for example, chlorite ion, iodite ion, bromite ion; a hypohalous acid ion including, for example, hypochlorite ion, hypoiodite ion, hypobromite ion; for example, nitric ion, nitrite ion, sulfate ion, sulfite ion, hydrogen sulfate ion, hydrogen sulfite ion, phosphate ion, phosphite ion, hydrogen phosphate ion, hydrogen phosphite ion, carbonate ion, hydrogen carbonate ion, borate ion, hydrogen borate ion, hexafluorophosphate ion, tetrafluoroborate ion, hydroxide ion; carboxylic-acid-derived anions including a saturated aliphatic carboxylic acid having 2 to 7 carbon atoms such as, for example, formic acid, acetic acid, propionic acid, butyric acid, isobutyric acid, valeric acid, isovaleric acid, pivalic acid, hexanoic acid and cyclohexanecarboxylic acid; a halogenated saturated aliphatic carboxylic acid having 2 to 7 carbon atoms such as, for example, trifluoroacetic acid, trichloroacetic acid, tribromoacetic acid, triiodoacetic acid, 3,3,3-trifluoropropionic acid, 3,3,3-trichloropropionic acid, pentafluoropropionic acid, pentachloropropionic acid, pentabromopropionic acid, pentaiodopropionic acid, 3,3,4,4,4-pentafluorobutyric acid, heptachlorobutyric acid, heptafluorobutyric acid, heptabromobutyric acid, heptaiodobutyric acid, heptafluoroisobutyric acid, heptachloroisobutyric acid, heptabromoisobutyric acid, heptaiodoisobutyric acid, nonafluorovaleric acid, nonachlorovaleric acid, nonabromovaleric acid, nonaiodovaleric acid, 6,6,6-trifluorohexanoic acid, 6,6,6-trichlorohexanoic acid, perfluorohexanoic acid, perchlorohexanoic acid, perbromohexanoic acid, periodohexanoic acid and perfluorocyclohexanecarboxylic acid; an aromatic carboxylic acid having 7 to 11 carbon atoms such as, for example, benzoic acid and naphthoic acid; a halogenated aromatic carboxylic acid having 7 to 11 carbon atoms such as, for example, pentafluorobenzoic acid, pentachlorobenzoic acid, pentabromobenzoic acid, pentaiodobenzoic acid, perfluoronaphthoic acid, perchloronaphthoic acid, perbromonaphthoic acid and periodonaphthoic acid; sulfonic-acid-derived anions including an alkylsulfonic acid having 1 to 6 carbon atoms such as, for example, methanesulfonic acid, ethanesulfonic acid, propanesulfonic acid, butansulfonic acid, pentanesulfonic acid and hexanesulfonic acid; a haloalkylsulfonic acid having 1 to 6 carbon atoms such as, for example, trifluoromethanesulfonic acid, trichloromethanesulfonic acid, tribromomethanesulfonic acid, pentafluoroethanesulfonic acid, pentachloroethanesulfonic acid, pentabromoethanesulfonic acid, pentaiodoethanesulfonic acid, heptafluoropropanesulfonic acid, heptachloropropanesulfonic acid, heptabromopropanesulfonic acid, heptaiodopropanesulfonic acid, nonafluorobutanesulfonic acid, nonachlorobutanesulfonic acid, nonabromobutanesulfonic acid, nonaiodobutanesulfonic acid, perfluoropentanesulfonic acid, perchloropentanesulfonic acid, perbromopentanesulfonic acid, periodopentanesulfonic acid, perfluorohexanesulfonic acid, perchlorohexanesulfonic acid and periodohexanesulfonic acid; a cycloalkylsulfonic acid such as, for example, cyclohexanesulfonic acid; an aromatic sulfonic acid having 6 to 10 carbon atoms such as, for example, benzenesulfonic acid, naphthalenesulfonic acid, p-toluenesulfonic acid and p-methoxybenzenesulfonic acid; a halogenated aromatic sulfonic acid having 6 to 10 carbon atoms such as, for example, pentafluorobenzenesulfonic acid, pentachlorobenzenesulfonic acid, pentabromobenzenesulfonic acid, pentaiodobenzenesulfonic acid, perfluoronaphthalenesulfonic acid, perchloronaphthalenesulfonic acid, perbromonaphthalenesulfonic acid and periodonaphthalenesulfonic acid; and the like.

The sulfonate ester according to the present invention can be produced, for example, as described bellow.

Namely, the desired sulfonate ester compound can be obtained by mixing (a) a compound having a sulfo group with an organic base, appropriately isolating the resulting salt if necessary, subsequently reacting the salt with (b) a compound having a group represented by the general formula [1].

Alternatively, (a) a compound having a sulfo group and (b) a compound having a group represented by the general formula [1] may be reacted in the presence of an organic base by dissolving in a suitable solvent.

Methods for producing various types of sulfonate ester compounds will be explained referring to [A] to [E] processes below.

[A] Process

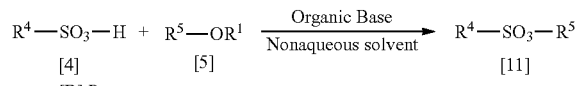

[B] Process

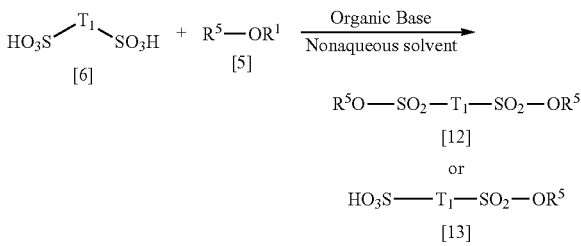

[C] Process

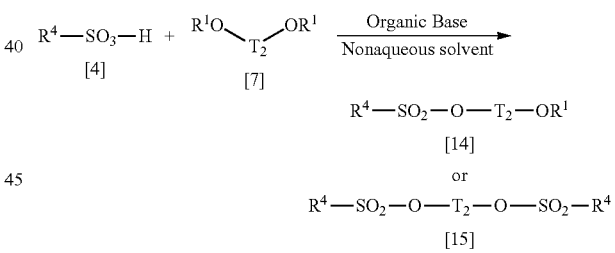

[D] Process

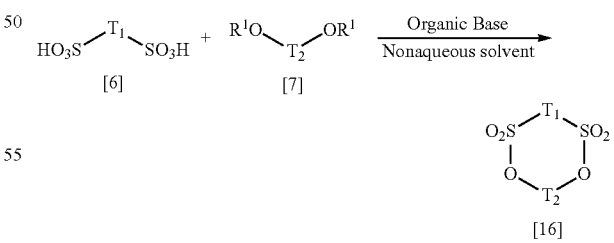

[E] Process

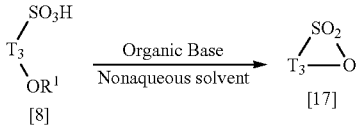

(wherein, $R^1$, $R^4$, $R^5$ and $T_1$ to $T_3$ are same as the above).

Namely, in [A] and [D] processes, the desired sulfonate ester compound (for example, the compounds represented by the general formulas [11] to [16]) can be obtained by mixing a compound represented by the general formula [4] or [6], 1 to 2 fold moles (hereinafter, in the description on [A] to [D] processes, "fold moles" means multiple number of moles of the organic base or the compound represented by the general formula [5] or [7] to be added to a raw material such as the compound represented by the general formula [4] or [6]) of an organic base and 0.8 to 5 fold moles of a compound represented by the general formula [5] or [7], relative to the compound represented by the general formula [4] or [6], and reacting at 0 to 100° C. for 0.5 to 12 hours with stirring in a suitable solvent.

Alternatively, the desired sulfonate ester compound may be also obtained by mixing a compound represented by the general formula [4] or [6] with said organic base in a suitable solvent in advance, removing the solvent by condensing, etc. if necessary, or precipitating the salt by adding a suitable poor solvent if necessary, then filtering to isolate the salt, and adding and reacting a compound represented by the general formula [5] or [7] to the salt which is formed by the compound represented by the general formula [4] or [6] and the organic base.

Namely, in [B] and [C] processes, the desired sulfonate ester compound (for example, the compounds represented by the general formulas [11] to [16]) can be obtained by adding a compound represented by the general formula [4] or [6], 1 to 4 fold moles of an organic base, and a compound represented by the general formula [5] or [7] into a suitable solvent at 0 to 10° C., and reacting for 0.5 to 12 hours with stirring.

It should be noted that the compound represented by the general formula [12] or [13] in [B] process and the compound represented by the general formula [14] or [15] in [C] process, which are the desired sulfonate ester compounds, can be obtained by appropriately adjusting amounts to be used of the compound represented by the general formula [4] or [6] as the starting material and the compound represented by the general formula [5] or [7]. That is, the compound represented by the general formula [12] may be obtained by reacting 2 to 10 fold moles of the compound represented by the general formula [5] relative to the compound represented by the general formula [6], whereas the compound represented by the general formula [13] may be obtained by reacting 0.2 to 0.5 fold moles of the compound represented by the general formula [5] relative to the compound represented by the general formula [6].

In addition, the compound represented by the general formula [14] may be obtained by reacting 1 to 5 fold moles of the compound represented by the general formula [7] relative to the compound represented by the general formula [4], whereas the compound represented by the general formula [15] can be obtained by reacting 0.2 to 0.5 fold moles of the compound represented by the general formula [7] relative to the compound represented by the general formula [4].

Alternatively, the desired sulfonate ester compound may be also obtained by mixing a compound represented by the general formula [4] or [6] with said organic base in a suitable solvent in advance, removing the solvent by condensing, etc. if necessary, or precipitating the salt by adding a suitable poor solvent if necessary, then filtering to isolate the salt, and adding and reacting a compound represented by the general formula [5] or [7] to the salt which is formed by the compound represented by the general formula [4] or [6] and the organic base.

Further, in [E] process, the compound represented by the general formula [16] as the desired sulfonate ester compound can be obtained by dissolving a compound represented by the general formula [8] in a suitable solvent, and adding 0.8 to 2 fold moles of an organic base relative to the compound represented by the general formula [8] thereto at 0 to 100° C., then reacting for 0.5 to 12 hours with stirring.

The reaction solvent to be used in the production method of the present invention is preferably nonaqueous one.

Specifically, the nonaqueous solvent includes aliphatic hydrocarbons such as, for example, hexane, heptane, octane, isooctane, nonane, decane, undecane, dodecane, tridecane, tetradecane, pentadecane, hexadecane, heptadecane, octadecane, cyclohexane, methylcyclohexane and ethylcyclohexane, or a mixture thereof (for example, paraffin, mineral spirit, and the like); halogenated hydrocarbons such as, for example, methylenechloride, methylenebromide, 1,2-dichloroethane and chloroform; aromatic hydrocarbons such as, for example, benzene, toluene and xylene; carbonates such as, for example, dimethyl carbonate, diethyl carbonate, ethylene carbonate, propylene carbonate; esters such as, for example, methyl acetate, ethyl acetate and butyl acetate; ketones such as, for example, acetone and methyl ethyl ketone; ethers such as, for example, diethyl ether, isopropyl ether, cyclopentyl methyl ether, tetrahydrofuran and dioxane; for example, acetonitrile; dimethylformamide; dimethylacetamide; dimethylsulfoxide; and the like. These solvents may be used alone or in a suitable combination of 2 or more types.

When the reaction solvent is used as mixed solvents, preferable combination thereof includes, for example, combination of acetonitrile and cyclohexane, combination of acetonitrile and toluene, and the like.

Reaction temperature is generally 0 to 150° C., and preferably 20 to 100° C.

Reaction time is generally 0.5 to 24 hours, and preferably 0.5 to 12 hours.

In addition, in [A] to [D] processes, the poor solvent to be used when the salt formed by a compound represented by the general formula [4] or [6] and an organic base is precipitated in advance may be any solvent, so long as the solvent can decrease a solubility of said salt, that is, the solvent can precipitate said salt. Specifically, the poor solvent includes aliphatic hydrocarbons such as, for example, hexane, heptane, octane, isooctane, nonane, decane, undecane, dodecane, tridecane, tetradecane, pentadecane, hexadecane, heptadecane, octadecane, cyclohexane, methylcyclohexane and ethylcyclohexane, or a mixture thereof (for example, paraffin, mineral spirit, and the like); halogenated hydrocarbons such as, for example, methylenechloride, methylenebromide, 1,2-dichloroethane and chloroform; aromatic hydrocarbons such as, for example, benzene, toluene and xylene; carbonates such as, for example, dimethyl carbonate, diethyl carbonate, ethylene carbonate and propylene carbonate; esters such as, for example, methyl acetate, ethyl acetate and butyl acetate; ketones such as, for example, acetone and methyl ethyl ketone; ethers such as, for example, diethyl ether, isopropyl ether, cyclopentyl methyl ether, tetrahydrofuran and dioxane; alcohols such as, for example, methanol, ethanol, n-propanol and isopropanol; acetonitrile; and the like. These solvents may be used alone or in a suitable combination of 2 or more types.

Post-treatment after the reaction may be carried out according to the post-treatment method commonly used in this field.

The compound represented by the general formula [8] may be suitably synthesized according to the known method described in published literatures (for example, WO 98/05634, etc.). Specifically, the compound can be produced, for example, as described below:

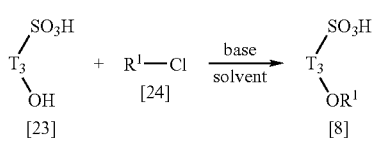

(wherein, $R_1$ and $T_3$ are same as the above)

Namely, the compound represented by the general formula [8] can be obtained by reacting an alcohol represented by the general formula [23] with 0.7 to 1.5 fold moles of the acid chloride represented by the general formula [24] relative to said alcohol in a solvent (e.g., halogenated hydrocarbons such as, for example, methylenechloride, methylenebromide, 1,2-dichloroethane, chloroform and carbon tetrachloride; ethers such as, for example, diethyl ether, diisopropyl ether, tetrahydrofuran and 1,2-dimethoxyethane; hydrocarbons such as, for example, pentane, hexane and heptanes; aromatic hydrocarbons such as, for example, benzene, toluene and nitrobenzene; for example, acetonitrile; dimethylsulfoxide; acetone; ethyl acetate; and the like) if necessary, in the presence of a base [e.g., amines such as, for example, triethylamine, trimethylamine, diisopropylethylamine, N,N-dimethylaniline and N,N-diethylaniline; nitrogen-containing aromatic hydrocarbons such as, for example, pyridine, 4-(N,N-dimethylamino)pyridine, imidazole and 2,6-lutidine; alcoxides such as, for example, sodium ethoxide, sodium methoxide and potassium tert-butoxide; alkali metal hydrides such as, for example, sodium hydride and potassium hydride; carbonate salts such as, for example, calcium carbonate, potassium carbonate, sodium carbonate, lithium carbonate, potassium hydrogencarbonate and sodium hydrogencarbonate; alkali metal hydroxides such as, for example, potassium hydroxide and sodium hydroxide; and the like] at −50 to 80° C. for 0.5 to 24 hours.

The compound represented by the general formulas [4] to [7] may be used by purchasing commercial products or by suitably synthesizing according to the known methods.

According to the production method of sulfonate ester compound of the present invention, a sulfonate ester can be produced efficiently in one step and in high yield, without having with problems such as long reaction time, low yield, many steps, etc. which were accompanied to the conventional methods.

In addition, although it was difficult to esterify an unsaturated aliphatic sulfonic acid such as allylsulfonic acid by the conventional methods, such sulfonic acids can be industrially produced by the method of the present invention.

Hereinafter, the present invention will be specifically explained referring to Examples and Comparative Examples, but the present invention is by no means limited thereto.

EXAMPLES

Example 1

Synthesis of Methylene Methanedisulfonate

In hexane (66 mL), diiodomethane (8.4 g, 31.4 mmol) and silver trifluoromethanesulfonate [TfOAg] (17.0 g, 66.2 mmol) were reacted at 65° C. for 8 hours with stirring to prepare methane ditriflate [$CF_3SO_2OCH_2OSO_2CF_3$]. To the resultant methane ditriflate solution, acetonitrile (66 mL) and pyridinium methanedisulfonate salt (10.0 g, 29.9 mmol) were added, and the mixture was reacted at 65° C. for further 2 hours. After completion of the reaction, precipitated silver iodide (13.4 g, 57.1 mmol) was removed by filtration. The resultant reaction liquid was condensed under the reduced pressure to obtain dark brown solid (21.3 g). This solid was purified by a silica gel column chromatography (ethyl acetate/hexane=⅓) to isolate the desired product of methylene methanedisulfonate in 73% yield (4.1 g, 21.8 mmol).

[Physical Properties Data]
$^1$H-NMR ($CD_3CN$) δ=5.30 (s, 2H), 5.97 (s, 2H).
$^{13}$C-NMR ($CD_3CN$) δ=68.9, 91.8.

Example 2

Synthesis of methyl 1-butanesulfonate

After 1-butanesulfonic acid (10 g, 0.072 mol) was dissolved in methylene chloride (50 mL), pyridine (11 g, 0.14 mol) was added dropwise thereto, and the mixture was reacted at room temperature for 2 hours. After completion of the reaction, the solvent was evaporated under the reduced pressure to dryness to obtain a crude product containing pyridinium 1-butanesulfonate salt. To a suspension of this crude product (5 g, 0.023 mol) in cyclohexane (50 mL), dimethyl sulfate (15 g, 0.12 mol) was added, and the mixture was reacted at 80° C. for 2 hours. The resultant reaction liquid was condensed under the reduced pressure to obtain the desired product of methyl 1-butanesulfonate. Quantitative analysis by $^1$H-NMR showed a conversion rate of 77%.

[Physical Properties Data]
$^1$H-NMR (DMSO-$d_6$) δ=0.90 (t, J=7 Hz, 3H), 1.42 (m, 2H), 1.66 (m, 2H), 3.31 (dd, J=7.6 Hz, 2H), 3.86 (s, 3H).

Example 3

Synthesis of Methyl Allylsulfonate

After allylsulfonic acid (10 g, 0.082 mol) was dissolved in methylene chloride (50 mL), pyridine (11 g, 0.14 mol) was added dropwise thereto, and the mixture was reacted at room temperature for 2 hours. After completion of the reaction, the solvent was evaporated under the reduced pressure to dryness to obtain a crude product containing pyridinium allylsulfonate salt. To a suspension of this crude product (5 g, 0.025 mol) in cyclohexane (50 mL), dimethyl sulfate (16 g, 0.12 mol) was added, and the mixture was reacted at 80° C. for 2 hours. The reaction liquid was condensed under the reduced pressure to obtain the desired product of methyl allylsulfonate. Quantitative analysis by $^1$H-NMR showed a conversion rate of 80%.

[Physical Properties Data]
$^1$H-NMR (DMSO-$d_6$) δ=3.89 (s, 3H), 4.14 (d, J=7 Hz, 2H), 5.46 (d, J=27 Hz), 5.49 (d, J=34 Hz, 1H), 5.8 (m, 1H).

Example 4

Synthesis of 2-(phenoxycarbonylamino) benzenesulfonic acid

To methylene chloride (50 mL), 2-aminobenzenesulfonic acid (10 g, 0.058 mol) and pyridine (10 g, 0.13 mol) were added, then phenyl chlorocarbonate (14 g, 0.087 mol) was further added dropwise thereto at room temperature, and the mixture was reacted for 2 hours. After completion of the reaction, the reaction mixture was washed with ion-exchanged water, condensed to dryness to obtain a crude product containing 2-(phenoxycarbonylamino)benzenesulfonic acid. To a suspension of this crude product (5 g, 0.01 mol) in cyclohexane (50 mL), dimethyl sulfate (6.4 g, 0.051 mol) was added, and the mixture was reacted at 80° C. for 2 hours. The reaction liquid was condensed under the reduced pressure to obtain the desired product of methyl 2-(phenoxycarbonylamino) benzenesulfonate. Quantitative analysis by $^1$H-NMR showed a conversion rate of 53%.

[Physical Properties Data]

$^1$H-NMR (DMSO-d$_6$) δ=4.00 (s, 3H), 7.2-7.6 (m, 4H), 7.7-8.1 (m, 5H), 9.30 (br s, 1H).

Example 5

Synthesis of methyl p-toluenesulfonate

To a suspension of p-toluenesulfonic acid dihydrate (10 g, 0.05 mol) in methylene chloride (50 mL), pyridine (5.1 g, 0.06 mol) was added dropwise, and the mixture was reacted at room temperature for 1 hour. After completion of the reaction, the solvent was evaporated to dryness under reduced pressure to obtain a crude product containing pyridinium p-toluenesulfonate salt. To a suspension of this crude product (5 g, 0.020 mol) in cyclohexane (50 mL), dimethyl sulfate (5.0 g, 0.040 mol) was added, and the mixture was reacted at 80° C. for 2 hours. The reaction liquid was condensed under the reduced pressure to obtain the desired product of methyl p-toluenesulfonate. Quantitative analysis by $^1$H-NMR showed a conversion rate of 90%.

[Physical Properties Data]

$^1$H-NMR (DMSO-d$_6$) δ=2.43 (s, 3H), 3.72 (s, 3H), 7.45 (d, J=8.4 Hz), 7.72 (d, J=8.4 Hz, 2H).

Example 6

Synthesis of methyl p-toluenesulfonate

To a suspension of p-toluenesulfonic acid dihydrate (10 g, 0.05 mol) in methylene chloride (50 mL), quinoline (8.3 g, 0.06 mol) was added dropwise, and the mixture was reacted at room temperature for 1 hour. After completion of the reaction, the solvent was evaporated to dryness under the reduced pressure to obtain a crude product containing quinolinium p-toluenesulfonate salt. To a suspension of this crude product (5 g, 0.016 mol) in cyclohexane (50 mL), dimethyl sulfate (4.2 g, 0.033 mol) was added, and the mixture was reacted at 80° C. for 2 hours. The reaction liquid was condensed under the reduced pressure to obtain the desired product of methyl p-toluenesulfonate. Quantitative analysis by $^1$H-NMR showed a conversion rate of 93%.

Example 7

Synthesis of methyl p-toluenesulfonate

To a suspension of p-toluenesulfonic acid dihydrate (10 g, 0.05 mol) in methylene chloride (50 mL), diphenylamine (10.8 g, 0.06 mol) was added dropwise, and the mixture was reacted at room temperature for 1 hour. After completion of the reaction, the solvent was evaporated to dryness under the reduced pressure to obtain a crude product containing diphenylammonium p-toluenesulfonate salt. To a suspension of this crude product (5 g, 0.011 mol) in cyclohexane (50 mL), dimethyl sulfate (3.0 g, 0.023 mol) was added, and the mixture was reacted at 80° C. for 2 hours. The reaction liquid was condensed under the reduced pressure to obtain the desired product of methyl p-toluenesulfonate. Quantitative analysis by $^1$H-NMR showed a conversion rate of 63%.

Example 8

Synthesis of Methylene Methanedisulfonate

In dimethyl carbonate (10 mL), methylenebis(chlorosulfate) [ClSO$_2$OCH$_2$OSO$_2$Cl] (1.5 g, 6.1 mmol) synthesized according to the ordinary method (for example, U.S. Pat. No. 4,649,209) and pyridinium methanedisulfonate salt (2.0 g, 6.0 mmol) were reacted at 55° C. for 3 hours with stirring. After completion of the reaction, precipitated pyridinium chlorosulfonate salt was removed by filtration, and the resultant reaction liquid was condensed under the reduced pressure to obtain a pale brown solid (2.0 g). Quantitative analysis of this solid by $^1$H-NMR showed 76% yield for the desired product of methylene methanedisulfonate.

[Physical Properties Data]

$^1$H-NMR (CD$_3$CN) δ=5.31 (s, 2H), 5.97 (s, 2H).

$^{13}$C-NMR (CD$_3$CN) δ=68.9, 91.8.

As obvious from the results of Example 3, even if esterification of an unsaturated aliphatic sulfonic acid such as allylsulfonic acid, etc. is carried out by a conventional method, the desired product cannot be obtained due to addition of hydrochloric acid as a by-product to the unsaturated bond, whereas, by using the production method of the present invention, an unsaturated aliphatic sulfonate ester such as allylsulfonate, etc. has become possible to be produced.

As obvious from the results of Examples 1 to 8, the desired sulfonate esters could be obtained in higher yield compared with that by a conventional method.

What is claimed is:

1. A method for producing a sulfonate ester compound represented by formula (11):

$$R^4-SO_2-OR^5 \quad (11),$$

wherein R$^4$ represents (i) a C$_{1-12}$ alkyl group optionally having one sulfo group or —SO$_2$—OR$^5$ as a substituent, (ii) a C$_{2-12}$ alkenyl group, or (iii) an aryl group optionally having a substituent selected from the group consisting of an amino group optionally substituted by a phenoxycarbonyl group and a C$_{1-2}$ alkyl group, where said aryl group is a group selected from the group consisting of a phenyl group, a naphthyl group, a phenanthryl group, and an anthryl group, and R$^5$ represents a C$_{1-12}$ alkyl group optionally having a group represented by formula (1):

$$-OR^1 \quad (1),$$

wherein R$^1$ represents sulfonyl group represented by formula (2) as a substituent:

$$-SO_2-R^2 \quad (2),$$

wherein R$^2$ represents a halogen atom, a C$_{1-12}$ fluoroalkyl group, or a C$_{1-12}$ alkoxy group, and the R$^4$ and the R$^5$ optionally form a group represented by a following formula:

$$-T_1-SO_2-O-T_2-,$$

wherein T$_1$ and T$_2$ represent each independently a C$_{1-8}$ alkylene chain, where the T$_1$ binds to an adjacent S atom and the T$_2$ binds to an adjacent O atom, so as to form a ring, the method comprising:

reacting (a) a compound having a sulfo group (—SO$_3$H), which is capable of forming a salt with an organic base, represented by formula (4):

$$R^4-SO_2-OH \quad (4),$$

wherein the R$^4$ is as defined above, and (b) a compound represented by formula (5):

wherein the $R^1$ represents a sulfonyl group represented by formula (2) as defined above, and the $R^5$ is as defined above, in the presence of an organic base, which is capable of forming a salt with said sulfo group.

2. The method according to claim 1,
wherein (a) the compound having a sulfo group represented by the formula (4) and the organic base are mixed, and then (b) the compound represented by the formula (5) is reacted therewith.

3. The method according to claim 1, wherein:
(a) the compound represented by the formula (4) is a disulfonic acid represented by formula (6):

wherein $T_1$ is a $C_{1-8}$ alkylene chain, and
at least one sulfonate ester compound obtained by said method is selected from the group consisting of a compound represented by formula (12) and a compound represented by formula (13):

and

wherein $R^5$ represents a $C_{1-12}$ alkyl group optionally having a group represented by the formula (1):

wherein $R^1$ represents a sulfonyl group represented by the formula (2) as a substituent:

wherein $R^2$ represents a halogen atom, a $C_{1-12}$ fluoroalkyl group, or a $C_{1-12}$ alkoxy group, as defined in claim 1 above.

4. The method according to claim 1, wherein:
b) the compound represented by the formula (5) is a compound represented by formula (7):

wherein each $R^1$ independently represents a sulfonyl group represented by the formula (2) as a substituent:

wherein the $R^2$ represents halogen atom, a $C_{1-12}$ fluoroalkyl group, or a $C_{1-12}$ alkoxy group,
$T_2$ is a $C_{1-8}$ alkylene chain, and
at least one sulfonate ester compound obtained by said method is selected from the group consisting of a compound represented by formula (14) and a compound represented by formula (15):

and

wherein $R^4$ represents
(i) a $C_{1-12}$ alkyl group optionally having one sulfo group or —$SO_2$—$OR^5$ as a substituent,
(ii) a $C_{2-12}$ alkenyl group, or
(iii) an aryl group optionally having a substituent selected from the group consisting of an amino group optionally substituted by a phenoxycarbonyl group and a $C_{1-2}$ alkyl group, where said aryl group is a group selected from the group consisting of a phenyl group, a naphthyl group, a phenanthryl group, and an anthryl group, as defined in claim 1 above.

5. The method according to claim 1, wherein:
(a) the compound represented by the formula (4) is a disulfonic acid represented by formula (6):

wherein $T_1$ is a $C_{1-8}$ alkylene chain,
(b) the compound represented by the formula (5) is a compound represented by formula (7):

wherein each $R^1$ independently represents a sulfonyl group represented by the formula (2) as a substituent:

wherein $R^2$ represents a halogen atom, a $C_{1-12}$ fluoroalkyl group, or a $C_{1-12}$ alkoxy group, and
$T_2$ is a $C_{1-8}$ alkylene chain, and
a sulfonate ester compound represented by formula (16) is obtained by the reaction:

6. The method according to claim 5, wherein the $T_1$ and the $T_2$ represent a methylene group.

7. The method according to claim 1, wherein the $R^1$ represents a chlorosulfonyl group or a trifluoromethanesulfonyl group.

8. The method according to claim 1, wherein the organic base is a secondary amine, a tertiary arm or a quaternary ammonium salt.

9. The method according to claim 8, wherein the secondary amine and the tertiary amine are an amine represented by formula (18):

wherein $R^7$ to $R^9$ each independently represent a hydrogen atom or an alkyl group, and the $R^7$ to the $R^9$ together with a nitrogen atom, to which these groups bind, optionally form a hetero ring, excepting a case when two or all of the $R^7$ to the $R^9$ are hydrogen atoms.

10. The method according to claim 8, wherein the tertiary amine is pyridine, collidine or lutidine.

11. The method according to claim 8, wherein quaternary ammonium salt is an ammonium salt represented by formula (19):

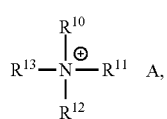 (19)

wherein $R^{10}$ to $R^{13}$ each independently represent an alkyl group or an aralkyl group, and A represents a counter anion, and further, three of the $R^{10}$ to the $R^{13}$ together with a nitrogen atom, to which these groups bind, optionally form a hetero ring.

12. The method according to claim 8, wherein the quaternary ammonium salt is pyridinium salt or imidazolium salt.

13. The method according to claim 11, wherein the A is a halide ion or a hydroxide ion.

14. The method according to claim 1, wherein the reacting step of (a) a compound having a sulfo group ($-SO_3H$) represented by the formula (4) and (b) compound represented by the formula (5) is carried out in a nonaqueous solvent.

15. The method according to claim 1, wherein a by-product is not removed from a reaction system.

* * * * *